United States Patent
Becker et al.

(10) Patent No.: US 6,822,120 B2
(45) Date of Patent: Nov. 23, 2004

(54) SULFONE LIVER X-RECEPTOR MODULATORS

(75) Inventors: Daniel P. Becker, Glenview, IL (US); Gary A. DeCrescenzo, St. Charles, MO (US); James W. Malecha, Libertyville, IL (US); Julie M. Miyashiro, Skokie, IL (US); Jennifer Ann Van Camp, Glencoe, IL (US); Joe T. Collins, Ballwin, MO (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 10/445,370

(22) Filed: May 23, 2003

(65) Prior Publication Data

US 2004/0048920 A1 Mar. 11, 2004

Related U.S. Application Data

(60) Provisional application No. 60/383,083, filed on May 24, 2002.

(51) Int. Cl.$^7$ .............................................. C07C 317/04
(52) U.S. Cl. ............................. 568/28; 568/18; 568/27; 568/32; 514/706; 514/708; 514/709
(58) Field of Search ............................. 568/18, 27, 28, 568/32; 514/706, 709

(56) References Cited

U.S. PATENT DOCUMENTS

| | | | |
|---|---|---|---|
| 3,637,803 A | * | 1/1972 | Tsung-Ying et al. .......... 560/11 |
| 5,011,851 A | | 4/1991 | Meanwell |
| 5,639,616 A | | 6/1997 | Liao et al. |
| 5,684,204 A | * | 11/1997 | Matthews ..................... 568/31 |
| 6,316,503 B1 | | 11/2001 | Li et al. |
| RE37,770 E | | 6/2002 | Elias et al. |
| 2001/0018428 A1 | | 8/2001 | Zablocki et al. |
| 2001/0020030 A1 | | 9/2001 | Stewart et al. |
| 2002/0013334 A1 | | 1/2002 | Robl et al. |
| 2002/0016364 A1 | | 2/2002 | Luchoomun et al. |
| 2002/0037872 A1 | | 3/2002 | Palle et al. |
| 2002/0045607 A1 | | 4/2002 | Beachy et al. |
| 2002/0048572 A1 | | 4/2002 | Shan et al. |
| 2002/0120137 A1 | | 8/2002 | Houze et al. |
| 2002/0165394 A1 | | 11/2002 | Dumas et al. |

FOREIGN PATENT DOCUMENTS

| | | |
|---|---|---|
| EP | 0 135 894 A2 | 4/1985 |
| EP | 0 558 062 A2 | 9/1993 |
| WO | WO 91/00277 | 1/1991 |
| WO | WO 91/00281 | 1/1991 |
| WO | WO 96/19493 | 6/1996 |
| WO | WO 96/34851 | 11/1996 |
| WO | WO 99/19300 | 4/1999 |
| WO | WO 00/54759 | 9/2000 |
| WO | WO 00/55118 | 9/2000 |
| WO | WO 00/56710 | 9/2000 |
| WO | WO 01/60818 A1 | 8/2001 |
| WO | WO 02/20463 A2 | 3/2002 |
| WO | WO 02/24632 A2 | 3/2002 |
| WO | WO 02/46141 A2 | 6/2002 |
| WO | WO 02/46172 A2 | 6/2002 |
| WO | WO 02/46181 A2 | 6/2002 |

OTHER PUBLICATIONS

CA:137:198704 abs of Molecular Endocrinology by Whitney et al 16(6) pp1378–1385 2002.*
CA:138:22685 abs of WO2003002118 Jan. 2003.*
CA:140:69940 abs of Arteriosclerosis, Thrombosisn and Vascular Biology by Lund et al 23(7) pp1169–1177 2003.*
CA:138:163703 abs of Diabetes by Stulnig et al 51(8) pp 2426–2433 2002.*
CA:139:359713 abs of Steroids by Fukuchi et al 68(7–8) pp 685–691 2003.*
CA:135:75010 abs of Steroids by Song et al 66(6) pp 473–9 2001.*

* cited by examiner

Primary Examiner—Shailendra Kumar

(57) ABSTRACT

The present invention is directed to selective LXR modulators, small molecule compounds corresponding to Formula I and is further directed to a process of treating a condition in a mammal that is modulated by LXR using a therapeutically effective dose of a compound of Formula I.

12 Claims, No Drawings

SULFONE LIVER X-RECEPTOR MODULATORS

REFERENCE TO RELATED APPLICATIONS

This application claims the benefit of U.S. provisional application Ser. No. 60/383,083, filed May 24, 2002, the entire disclosure of which is herein incorporated by reference.

BACKGROUND

Liver X-receptors (LXRs) are nuclear receptors that regulate the metabolism of several important lipids, including cholesterol and bile acids. Most of the cholesterol in plasma is transported on three major lipoprotein classes; VLDL cholesterol (VLDL-C), LDL cholesterol (LDL-C) and HDL cholesterol (HDL-C). Total cholesterol is the sum of all three lipoproteins. Both VLDL-C and LDL-C are associated with atherogenic processes while HDL-C is believed to facilitate cholesterol removal from tissues (e.g. atherosclerotic plaques) and thus have a protective effect on coronary heart disease.

LXR represents a novel intervention point to regulate the reverse cholesterol transport (RCT) pathway, i.e., the removal of cholesterol from peripheral tissues/cells and subsequent uptake via the liver for disposal. Removal of cellular cholesterol requires active transport of free cholesterol across the plasma membrane and onto HDL particles. This transfer of cholesterol from inside the cell and onto HDL in the plasma is mediated by ATP binding cassette 1 (ABCA1) transporter protein. The observation that LXR is a key transcriptional activator of ABCA1 in the macrophage, suggests that induction of LXR will lead to an increase in cholesterol efflux from the macrophage. In addition, it is known that LXR regulates the induction of other genes involved in RCT such as apoE and cholesterol ester transport protein (CETP), suggesting that activating the LXR pathway should also lead to increased uptake of cholesterol by the liver. Thus, activation of LXR by a small molecule ligand will lead to an up-regulation of ABCA1 and induction of the reverse cholesterol transport pathway thereby increasing cholesterol efflux to HDL-C and reducing the cholesterol content of atherosclerotic plaques.

SUMMARY OF THE INVENTION

In general, the present invention is directed to LXR modulators being small-molecule compounds corresponding to Formula (I) and the isomers, tautomers, salts and prodrugs thereof:

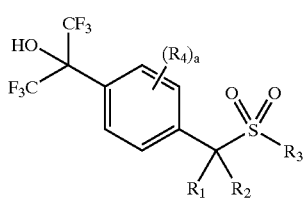

Formula (I)

wherein:

$R_1$ and $R_2$ are independently hydrogen or optionally substituted alkyl, alkenyl, aryl, acyl, or alkaryl;
$R_3$ is optionally substituted alkyl or aryl;
each $R_4$ is independently hydrogen, alkyl, aryl, heteroaryl, hydroxy, alkoxy, cyano, nitro, amino, alkenyl, alkynyl, amido, alkylcarbonyl, alkoxycarbonyl, aryloxycarbonyl, haloalkylcarbonyl, alkylthiocarbonyl, arylthiocarbonyl, alkyl optionally substituted with one or more substituent selected from lower alkyl, halogen, hydroxyl, haloalkyl, cyano, nitro, carboxyl, amino, alkoxy and aryl, or aryl optionally substituted with one or more substituent selected from hydrogen, halogen, haloalkyl, hydroxy, lower alkyl, alkoxy, methylene dioxy, ethylenedioxy, cyano, nitro, alkylthio, alkylsulfonyl, sulfonic acid, sulfonamide, carboxyl derivatives, amino, aryl and heteroaryl; and
a is 0–4.

DETAILED DESCRIPTION OF THE PREFERRED EMBODIMENTS

The present invention is generally directed to small molecule compounds corresponding to Formula (I) and each of the other formulae disclosed herein, the isomers, tautomers, salts and prodrugs thereof and their use as LXR modulators. In particular, the LXR modulators may be used in the treatment of atherosclerosis, dyslipidemia, diabetes, Alzheimers disease or Niemann-Pick disease.

In general, $R_1$ and $R_2$ are independently hydrogen or optionally substituted alkyl, alkenyl, aryl, acyl, or alkaryl. In one embodiment, the substituent(s) of the optionally substituted alkyl, alkenyl, aryl, acyl, or alkaryl are selected from halogen, haloalkyl, hydroxy, hydroxyalkyl, lower alkyl, alkoxy, cyano, nitro, alkylthio, alkylsulfonyl, sulfonic acid, sulfonamide, carboxyl derivatives, amino, aryl and heteroaryl. In another embodiment, the substituent(s) of the optionally substituted alkyl, alkenyl, aryl, acyl, or alkaryl are selected from halogen, haloalkyl, hydroxy, hydroxyalkyl, lower alkyl, alkoxy, cyano, nitro, alkylthio, amino, aryl and heteroaryl. For example, $R_1$ and $R_2$ may independently be hydrogen, methyl, substituted methyl (e.g., trifluoromethyl), ethyl, substituted ethyl (e.g., trifluoroethyl and 2-methoxyethyl), propyl and the like; in one such embodiment, $R_1$ and $R_2$ are independently methyl, ethyl, trifluoromethyl, trifluoroethyl or 2-methoxyethyl. Alternatively, one of $R_1$ and $R_2$ may be optionally substituted cycloalkyl; for example, one of $R_1$ and $R_2$ may be cyclopropyl, cyclobutyl, cyclopentyl, etc., optionally substituted with any of the aforementioned substituents while the other is hydrogen or optionally substituted alkyl. Alternatively, one of $R_1$ and $R_2$ may be acyl; for example, one of $R_1$ and $R_2$ may be benzoyl or pivaloyl while the other is hydrogen or optionally substituted alkyl. Alternatively, one of $R_1$ and $R_2$ may be benzyl or other alkaryl optionally substituted with halogen, hydroxy, alkoxy and the like; for example, $R_1$ may be benzyl, 4-methylbenzyl, 4-ethoxybenzyl, 4-methoxybenzyl, 4-halobenzyl, 2-halobenzyl, 3,4-dihalobenzyl and the like.

In general, $R_3$ is optionally substituted alkyl or aryl. In one embodiment, $R_3$ is selected from the group consisting of $(C_1-C_7)$alkyl, cycloalkyl, aryl, or aryl optionally substituted with one or more substituent selected from hydrogen, halogen, haloalkyl, hydroxy, lower alkyl, alkoxy, cyano, nitro, alkylthio, alkylsulfonyl, sulfonic acid, sulfonamide, carboxyl derivatives, amino, aryl and heteroaryl. In another embodiment, $R_3$ is phenyl, toluyl, naphthyl, or other substituted phenyl (with the substituents be selected from such substituents). In another embodiment, $R_3$ is naphthyl or substituted naphthyl (with the substituents be selected from such substituents).

Each $R_4$ is independently selected from the list of substitutents as described above in connection with Formula 1. In one embodiment, a is zero (stated another way, each $R_4$ is hydrogen). In another embodiment, a is greater than zero and $R_4$ is other than hydrogen; for example, $R_4$ may be optionally substituted alkyl, alkenyl, alkynyl, hydroxy, alkoxy, cyano, nitro, amino, or amido. In addition, when a is at least two and each such $R_4$ is other than hydrogen, two of the $R_4$ substituents may combine to form a fused ring (e.g., wherein the two $R_4$ substituents define a fused ring comprising a methylene dioxy or ethylene dioxy linkage).

As noted, a may be 0 to 4. In general, however, a will typically be 0 to 2. In some embodiments, a will be 0 or 1. In other embodiments, a will be 1 and $R_4$ will be as previously defined herein.

In one embodiment, the present invention is directed to compounds corresponding to Formula I; wherein a is 0–4, one of $R_1$ and $R_2$ is hydrogen, one of $R_1$ and $R_2$ is other than hydrogen, and $R_3$, $R_4$ are as defined in connection with Formula I.

In another embodiment, the present invention is directed to compounds corresponding to Formula I; wherein a is 0–4, $R_1$ and $R_2$ are both hydrogen, and $R_3$, $R_4$ are as defined in connection with Formula I.

Another aspect of the present invention are the prodrugs of the compounds corresponding to the formulae disclosed herein, which are converted under physiological conditions to the biologically active drug by any of a number of chemical and biological mechanisms. In general terms, these prodrug conversion mechanisms are hydrolysis, reduction, oxidation, and elimination.

A further aspect of the invention encompasses conversion of the prodrug to the biologically active drug by elimination of the prodrug moiety. Generally speaking, in this embodiment the prodrug moiety is removed under physiological conditions with a chemical or biological reaction. The elimination results in removal of the prodrug moiety and liberation of the biologically active drug. Any compound of the present invention corresponding to any of the formulas disclosed herein may undergo any combination of the above detailed mechanisms to convert the prodrug to the biologically active compound. For example, a particular compound may undergo hydrolysis, oxidation, elimination, and reduction to convert the prodrug to the biologically active compound. Equally, a particular compound may undergo only one of these mechanisms to convert the prodrug to the biologically active compound.

The compounds of the present invention can exist in tautomeric, geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of any of the formulae disclosed herein. The terms "cis" and "trans", as used herein, denote a form of geometric isomerism in which two carbon atoms connected by a double bond will each have a hydrogen atom on the same side of the double bond ("cis") or on opposite sides of the double bond ("trans"). Some of the compounds described contain alkenyl groups, and are meant to include both cis and trans or "E" and "Z" geometric forms.

Furthermore, some of the compounds described contain one or more stereocenters and are meant to include R, S, and mixtures or R and S forms for each stereocenter present.

Formulation

Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, β-hydroxybutyric, galactaric, and galacturonic acids.

Suitable pharmaceutically-acceptable base addition salts of compounds used in connection with the present invention include metallic ion salts and organic ion salts. More preferred metallic ion salts include, but are not limited to, appropriate alkali metal (group Ia) salts, alkaline earth metal (group IIa) salts and other physiological acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound of the present invention. Pharmaceutically acceptable esters include, but are not limited to, the alkyl esters of the LXR modulators.

The Liver X-Receptor (LXR) modulators described in the present invention may be used to treat, prevent or reduce atherosclerosis. Without being bound by any particular theory, it is presently believed that activation of LXR by a small molecule ligand will lead to an up-regulation of ABCA1 and induction of the reverse cholesterol transport pathway thereby increasing cholesterol efflux to HDL-C and reducing the cholesterol content of atherosclerotic plaques.

Administration

For methods of prevention, the subject is any human or animal subject, and preferably is a subject that is in need of prevention and/or treatment of atherosclerosis. The subject may be a human subject who is at risk for atherosclerosis. The subject may be at risk for atherosclerosis due to genetic predisposition, lifestyle, diet, exposure to disorder-causing agents, exposure to pathogenic agents and the like.

In general, therefore, one aspect of the present invention is the administration of a composition comprising an Liver X-Receptor modulator or a pharmaceutically acceptable salt for the treatment, prevention or removal of cholesterol deposition in vessel walls. The amount of LXR modulator that is used will generally be in the range of about 0.001 to about 100 milligrams per day per kilogram of body weight of the subject (mg/day·kg), more preferably from about 0.05 to about 50 mg/day·kg, even more preferably from about 0.1 to about 10 mg/day·kg. Those skilled in the art, however, will appreciate that dosages may also be determined with guidance from Goodman & Goldman's *The Pharmacological Basis of Therapeutics*, Ninth Edition (1996), Appendix II, pp. 1707–1711 and from Goodman & Goldman's *The Pharmacological Basis of Therapeutics*, Tenth Edition (2001), Appendix II, pp. 475–493. In addition, the LXR modulators of the present invention may be provided in a therapeutic composition so that the preferred amount is supplied by a single dosage, a single capsule for example, or, by up to four, or more, single dosage forms.

The LXR pharmaceutical composition(s), analog, hydrolysis product, metabolite or precursor may be administered enterally and parenterally. Parenteral administration includes subcutaneous, intramuscular, intradermal, intramammary, intravenous, and other administrative methods known in the art. Enteral administration includes solution, tablets, sustained release capsules, enteric coated capsules, and syrups. When administered, the pharmaceutical composition may be at or near body temperature.

The phrases "therapeutically-effective" and "effective for the treatment, prevention, or reduction", are intended to qualify the amount of each LXR agent and for use in the LXR therapy which will achieve the goal of reduction of the severity and/or frequency of incidence of atherosclerosis associated symptoms, while avoiding adverse side effects typically associated with alternative therapies.

In particular, the pharmaceutical composition of an LXR modulator and in connection with the method(s) of the present invention can be administered orally, for example, as tablets, coated tablets, dragees, troches, lozenges, gums, aqueous or oily suspensions, dispersible powders or granules, emulsions, hard or soft capsules, or syrups or elixirs.

Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, maize starch, or alginic acid; binding agents, for example starch, gelatin or acacia, and lubricating agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredients are mixed with an inert solid diluent, for example, calcium carbonate, calcium phosphate or kaolin, or as soft gelatin capsules wherein the active ingredients are present as such, or mixed with water or an oil medium, for example, peanut oil, liquid paraffin, or olive oil.

Aqueous suspensions can be produced that contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate.

The aqueous suspensions may also contain one or more preservatives, for example, ethyl or n-propyl p-hydroxybenzoate, one or more coloring agents, one or more flavoring agents, or one or more sweetening agents, such as sucrose or saccharin.

Oily suspensions may be formulated by suspending the active ingredients in an omega-3 fatty acid, a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavoring and coloring agents, may also be present. Syrups and elixirs containing the novel combination may be formulated with sweetening agents, for example glycerol, sorbitol or sucrose. Such formulations may also contain a demulcent, a preservative and flavoring and coloring agents.

The subject pharmaceutical composition of LXR modulators in connection with the present inventive method can also be administered parenterally, either subcutaneously, or intravenously, or intramuscularly, or intrasternally, or by infusion techniques, in the form of sterile injectable aqueous or olagenous suspensions. Such suspensions may be formulated according to the known art using those suitable dispersing of wetting agents and suspending agents which have been mentioned above, or other acceptable agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, n-3 polyunsaturated fatty acids may find use in the preparation of injectables.

The subject pharmaceutical composition of LXR modulators and in connection with the present inventive method can also be administered by inhalation, in the form of aerosols or solutions for nebulizers, or rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols.

The pharmaceutical compositions of LXR modulators and in connection with the present inventive method can also be administered topically, in the form of patches, creams, ointments, jellies, collyriums, solutions or suspensions. Of course, the compositions of the present invention can be administered by routes of administration other than topical administration. Also, as mentioned above, the LXR modulators and may be administered separately, with each agent administered by any of the above mentioned administration routes. For example, the LXR modulators may be administered orally in any or the above mentioned forms (e.g. in capsule form) while the is administered topically (e.g. as a cream).

Daily dosages can vary within wide limits and will be adjusted to the individual requirements in each particular case. In general, for administration to adults, an appropriate daily dosage has been described above, although the limits that were identified as being preferred may be exceeded if expedient. The daily dosage can be administered as a single dosage or in divided dosages.

The pharmaceutical composition may optionally contain, in addition to the LXR modulator, another lipid modulating agent such as a statin, resin, niacin or other cholesterol absorption inhibitor. Alternatively, these other lipid modulating agents may be administered separately but in conjunction with the LXR modulator as part of a co-therapy.

Synthesis

Compounds of the present invention can be prepared by bromination of (i) to give (ii). Benzyl bromide (ii) can be substituted with a sulfide followed by oxidation to form sulfone (iii) (Scheme 1).

Other compounds of the present invention can be prepared from sulfone (iii). Conversion of sulfone (iii) to silyl ether (iv) followed by acylation or mono or bis-alkylation and de-protection can give the sulfones (v) and (vi) respectively (Scheme 2).

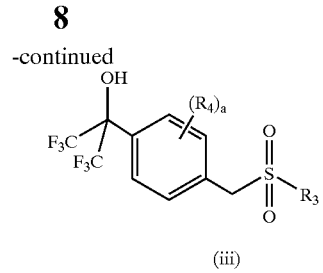

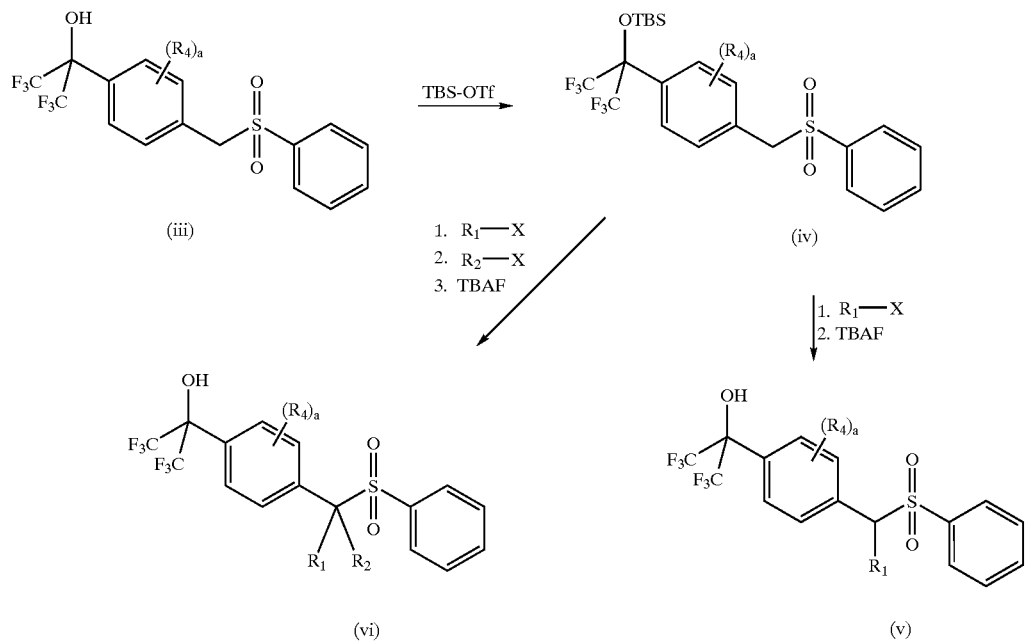

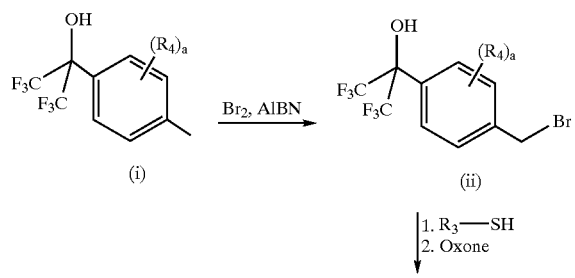

Definitions

The term "acyl," as used herein alone or as part of another group, denotes the moiety formed by removal of the hydroxyl group from the —COOH group of an organic carboxylic acid, e.g., RC(O)— wherein R is $R_a$, $R_aO$—, $R_aS$—, or $R_aR_bN$—, $R_a$ and $R_b$ are independently hydrogen, hydrocarbyl, substituted hydrocarbyl, or heterocyclo and "—" denotes the point of attachment.

The term "acylamino," as used herein alone or as part of another group, denotes an acyl group as defined above, bonded through a nitrogen atom, e.g., RC(O)N($R_c$)— wherein R is as defined in connection with the term "acyl", $R_c$ is hydrogen, hyrocarbyl, or substituted hydrocarbyl, and "—" denotes the point of attachment.

The term "acyloxy" as used herein alone or as part of another group, denotes an acyl group as defined above, bonded through an oxygen atom (—O—), e.g., RC(O)O— wherein R is as defined in connection with the term "acyl" and "—"denotes the point of attachment.

The term "acylthio" as used herein alone or as part of another group, denotes an acyl group as defined above, bonded through a sulfur atom (—S—), e.g., RC(O)S— wherein R is as defined in connection with the term "acyl" and "—" denotes the point of attachment.

The term "amino" as used herein alone or as part of another group shall denote a primary, secondary or tertiary amine which may optionally be hydrocarbyl, substituted hydrocarbyl or heteroatom substituted. Specifically included are secondary or tertiary amine nitrogens which are members of a heterocyclic ring. Also specifically included, for example, are secondary or tertiary amino groups substituted by an acyl moiety.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The term "heteroatom" shall mean atoms other than carbon and hydrogen.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" shall mean aryl or heteroaromatic.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

As used herein, an "effective amount" or "therapeutically effective amount" means the dose or effective amount to be administered to a patient and the frequency of administration to the subject which is sufficient to obtain a therapeutic effect as readily determined by one of ordinary skill in the art, by the use of known techniques and by observing results obtained under analogous circumstances. The dose or effective amount to be administered to a patient and the frequency of administration to the subject can be readily determined by one of ordinary skill in the art by the use of known techniques and by observing results obtained under analogous circumstances. In determining the effective amount or dose, a number of factors are considered by the attending diagnostician, including but not limited to, the potency and duration of action of the compounds used; the nature and severity of the illness to be treated as well as on the sex, age, weight, general health and individual responsiveness of the patient to be treated, and other relevant circumstances.

The phrase "therapeutically effective" indicates the capability of an agent to prevent, or reduce the severity of, the disorder or its undesirable symptoms, while avoiding adverse side effects typically associated with alternative therapies. The term "pharmacologically effective amount" shall mean that amount of a drug or pharmaceutical agent that will elicit the biological or medical response of a tissue, system, animal or human that is being sought. This amount can be a therapeutically effective amount.

The term "pharmaceutically acceptable" is used herein to mean that the agent or adjuvant is appropriate for use in a pharmaceutical product. Pharmaceutically acceptable cations include metallic ions and organic ions. More preferred metallic ions include, but are not limited to, appropriate alkali metal salts, alkaline earth metal salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Exemplary pharmaceutically acceptable acids include, without limitation, hydrochloric acid, hydroiodic acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid oxalacetic acid, fumaric acid, propionic acid, aspartic acid, glutamic acid, benzoic acid, and the like.

The term "subject" for purposes of treatment includes any human or animal subject who is in need of the treatment, prevention or inhibition of an LXR-mediated disorder. The subject is typically a human subject.

Other embodiments within the scope of the embodiments herein will be apparent to one skilled in the art from consideration of the specification or practice of the invention as disclosed herein. It is intended that the specification be considered to be exemplary only, with the scope and spirit of the invention being indicated by the embodiments.

As various changes could be made in the above methods and compositions without departing from the scope of the invention, it is intended that all matter contained in this application shall be interpreted as illustrative and not in a limiting sense.

The following examples illustrate the invention.

EXAMPLE 1

1,1,1,3,3,3-Hexafluoro-2-{4-[(phenylsulfonyl)methyl]phenyl}propan-2-ol

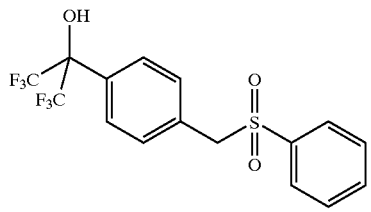

Step 1

2-[4-(Bromomethyl)phenyl]-1, 1,1,3,3,3-hexafluoropropan-2-ol 1,1,1,3,3,3-hexafluoro-2-(4-methylphenyl)propan-2-ol (Lancaster, 25 g, 96.8 mmol) was suspended in $CCl_4$ (125 mL). To the suspension was added NBS (17.2 g, 96.7 mmol) and AIBN (20 mg, 0.12 mmol). The reaction was heated at reflux for 2 h and cooled to ambient temperature over 48 h. The reaction mixture was filtered through Celite and concentrated in vacuo. The solid was dissolved in $Et_2O$ and filtered. Concentration of the mother liquor afforded the title bromide as a yellow oil (30.0 g, 92%). MS (ES+) m/z 338 (MH+).

Step 2

1,1,1,3,3,3-Hexafluoro-2-{4-[(phenylsulfonyl)methyl]phenyl}propan-2-ol

The product from step 1 (660 mg, 1.8 mmol), thiophenol (154 mg, 1.4 mmol), and powdered $K_2CO_3$ (487 mg, 3.5 mmol) were combined in THF (8 mL) and agitated at room temperature over 18 h. PS-trisamine resin (500 mg, 1.5 mmol) was added and the reaction agitated an additional 18 h. The solution was filtered through Celite and concentrated in vacuo to afford the intermediate sulfide as a yellow oil (690 mg). The sulfide was dissolved in 4:3 THF:$H_2O$ (7 mL) and Oxone® (2.2 g, 3.6 mmol) was added. After stirring 48 h, the reaction mixture was diluted with ethyl acetate/water. The layers were separated and the organic phase was washed with saturated $NaHCO_3$, followed by brine. The organics were dried ($MgSO_4$), filtered, and concentrated in vacuo. Purification by flash chromatography (8:1 hexanes/EtOAc) afforded the title compound as a white solid (290 mg, 52%). MS (ES+) m/z 399 (MH+).

EXAMPLE 2

1,1,1,3,3,3-Hexafluoro-2-(4-{[(4-methylphenyl)sulfonyl]methyl}phenyl)propan-2-ol

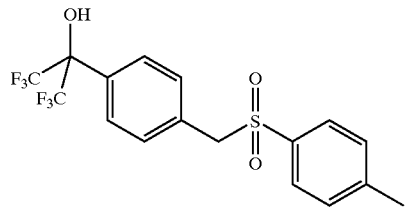

Prepared in the manner of Example 1 except p-thiocresol was substituted for thiophenol. Purification by flash chromatography (8:1 hexanes/EtOAc) afforded the title compound as a white solid (50%): mp=129° C. $^1$H NMR (CDCl$_3$) δ 7.56 (d, 2H), 7.40 (d, 2H), 7.14 (t, 4H), 4.24 (s, 2H), 3.54 (br s, 1H), 2.35 (s, 3H). for $C_{17}H_{14}O_3F_6S$: C, 49.52; H, 3.42. Found: C, 49.46; H, 3.11. HRMS (MH+) Calc.: 413.0646. Found: 413.0650.

EXAMPLE 3

1,1,1,3,3,3-Hexafluoro-2-{4-[(2-naphthylsulfonyl)methyl] phenyl}propan-2-ol

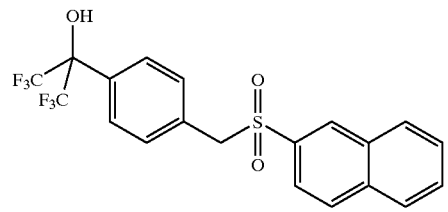

Prepared in the manner of Example 1 except 2-naphthalenethiol was substituted for thiophenol. Purification by flash chromatography (8:1 hexanes/EtOAc) afforded the title compound a white solid (47%): mp=148° C. $^1$H NMR (CDCl$_3$) δ 8.03 (br s, 1H), 7.82 (t, 2H), 7.75 (d, 1H), 7.60 (t, 1H), 7.52 (m, 4H) 7.11 (d, 2H), 4.33 (s, 2H), 3.50 (br s, 1H). Anal. Calc. for $C_{20}H_{14}O_3SF_6$: C, 53.57 H, 3.15. Found: C, 53.42; H, 2.92. HRMS (MH+) Calc.: 449.0646. Found: 449.0664.

EXAMPLE 4

2-(4-{[(4-Bromophenyl)sulfonyl]methyl}phenyl)-1,1,1,3,3,3-hexafluoropropan-2-ol

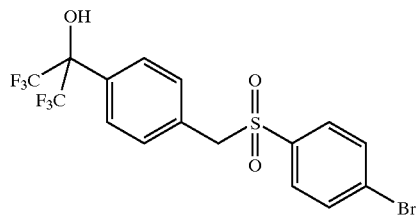

Prepared in the manner of Example 1 except 4-bromothiophenol was substituted for thiophenol. Purification by reverse phase HPLC using a gradient elution of 60:40H$_2$O/TFA:CH$_3$CN to 0:100H$_{20}$/TFA:CH$_3$CN at 254 nm afforded the title compound as a white solid (51%): mp=126° C. $^1$H NMR (CDCl$_3$) δ 7.58 (d, 2H), 7.50 (d, 2H), 7.36 (d, 2H), 7.13 (d, 2H), 4.26 (s, 2H). Anal. Calc. for C$_{16}$H$_{11}$O$_3$F$_6$SBr: C, 40.27; H, 2.32. Found: C, 40.05; H, 2.26. HRMS (MH$^+$) Calc.: 476.9595. Found: 476.9601.

EXAMPLE 5

2-(4-{[(2-Bromophenyl)sulfonyl]methyl}phenyl)-1,1,1,3,3,3-hexafluoropropan-2-ol

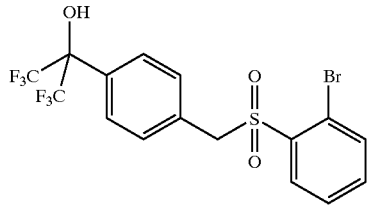

Prepared in the manner of Example 1 except 2-bromothiophenol was substituted for thiophenol. Purification by flash chromatography (8:1 hexanes/EtOAc) afforded the title compound a white solid (33%): mp=124° C. $^1$H NMR (CDCl$_3$) δ 7.68 (t, 2H), 7.52 (d, 2H), 7.34 (td, 1H), 7.23 (m, 3H), 4.63 (s, 2H), 3.48 (br s, 1H). Anal. Calc. for C$_{16}$H$_{11}$O$_3$SF$_6$Br: C, 40.26; H, 2.32. Found: C, 40.11; H, 2.25. HRMS (M+NH$_4$$^+$) Calc.: 493.9860. Found: 493.9893.

EXAMPLE 6

2-(4-{[(3-Bromophenyl)sulfonyl]methyl}phenyl)-1,1,1,3,3,3-hexafluoropropan-2-ol

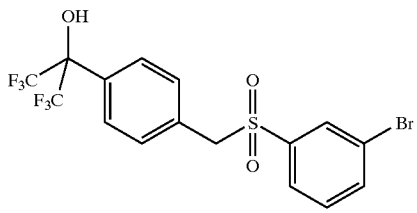

Prepared in the manner of Example 1 except 3-bromothiophenol was substituted for thiophenol. Purification by reverse phase HPLC using a gradient elution of 60:40H$_2$O/TFA:CH$_3$CN to 0:100H$_2$O/TFA:CH$_3$CN at 254 nm afforded the title compound as a white solid (59%): mp=121° C. $^1$H NMR (CDCl$_3$) δ 7.66 (m, 2H), 7.59 (d, 2H), 7.45 (dt, 1H), 7.23 (t, 1H), 7.15 (d, 2H), 4.27 (s, 2H). Anal. Calc. for C$_{16}$H$_{11}$OSBrF$_6$: C, 40.27; H, 2.32. Found: C, 40.17; H, 2.22. HRMS (M$^+$) Calc.: 475.9516. Found: 475.9478.

EXAMPLE 7

2-(4-{[(4-Chlorophenyl)sulfonyl]methyl}phenyl)-1,1,1,3,3,3-hexafluoropropan-2-ol

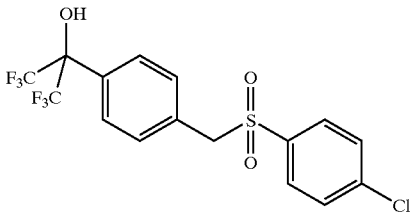

Prepared in the manner of Example 1 except 4-chlorothiophenol was substituted for thiophenol. Purification by flash chromatography (8:1 hexanes/EtOAc) afforded the title compound a white solid (37%): mp=112° C. $^1$H NMR (CDCl$_3$) δ 7.57 (d, 2H), 7.44 (d, 2H), 7.33 (d, 2H), 7.13 (d, 2H), 4.26 (s, 2H). Anal. Calc. for C$_{16}$H$_{11}$O$_3$SF$_6$Cl+ 0.4H$_2$O: C, 43.68; H, 2.70. Found: C, 43.56; H, 2.66. HRMS (M+NH$_4$$^+$) Calc.: 450.0365. Found: 450.0372.

EXAMPLE 8

1,1,1,3,3,3-Hexafluoro-2-{4-[1-(phenylsulfonyl)ethyl]phenyl}propan-2-ol

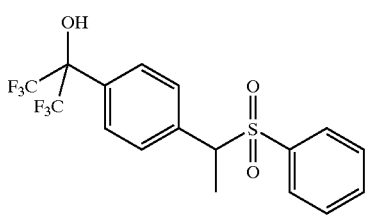

Step 1

Tert-Butyl(dimethyl)[2,2,2-trifluoro-1-{4-[(phenylsulfonyl)methyl]phenyl}-1-(trifluoromethyl)ethoxy]silane 1,1,1,3,3,3-hexafluoro-2-{4-[(phenylsulfonyl)methyl]phenyl}propan-2-ol (9.9 g, 24.8 mmol) was dissolved in CH$_2$Cl$_2$ (100 mL) under agron and cooled to 0° C. Triethylamine (5.1 mL, 36.5 mmol) was added followed by tert-butyldimethylsilyl triflurormethanesulfonate (6.3 mL, 27.4 mmol). The reaction was allowed to warm to room temperature and stirred over 18 h. After quenching with water, the reaction was diluted with CH$_2$Cl$_2$. The organic phase was washed with brine, dried (MgSO$_4$), and concentrated in vacuo. Purification by flash chromatography (7:1 hexanes/EtOAc) afforded the title compound as a yellow solid (9.8 g, 77%). MS (ES+) m/z 513(MH$^+$).

Step 2

Tert-Butyl(dimethyl)[2,2,2-trifluoro-1-{4-[1-(phenylsulfonyl)ethyl]phenyl}-1-(trifluoromethyl)ethoxy]silane The product from step 1 (153 mg, 0.3 mmol) was dissolved in anhydrous THF (1.5 mL) under argon and cooled to −78° C. 1.6 M BuLi solution in hexanes (0.2 mL, 0.32 mmol) was added to the cooled solution. The reaction was allowed to warm to room temperature then cooled to −78° C. and iodomethane (0.02 mL, 0.32 mmol) was added. The reaction was warmed to ambient temperature and monitored by thin layer chromatography. After 2.5 h at ambient temperature, the reaction was quenched with saturated NH$_4$Cl and diluted with ethyl acetate. The layers were separated and the organic phase was washed with brine. The organics were dried (MgSO$_4$) and concentrated in vacuo. Purification by flash chromatography (7:1 hexanes/EtOAc) afforded the title compound as a white solid (120 mg, 76%). MS (ES+) m/z 527 (MH$^+$).

Step 3

1,1,1,3,3,3-Hexafluoro-2-{4-[1-(phenylsulfonyl)ethyl] phenyl}propan-2-ol

The product from step 2 (120 mg, 0.23 mmol) was dissolved in anhydrous THF (2 mL) under argon and cooled to 0° C. 1 M tetrabutylammonium fluoride solution in THF (0.5 mL, 0.5 mmol) was added and the reaction stirred for 30 min. The reaction was quenched at 0° C. with saturated NH$_4$Cl and diluted with ethyl acetate. The layers were separated and the organic phase was washed with brine, dried (MgSO$_4$), and concentrated in vacuo. Purification by reverse phase HPLC using a gradient elution of 60:40H$_2$O/TFA:CH$_3$CN to 0:100H$_2$O/TFA:CH$_3$CN at 254 nm afforded the title compound as a white solid (81 mg, 86%): mp=136° C. $^1$H NMR (CDCl$_3$) δ 7.48–7.41 (m, 3H), 7.37 (d, 2H), 7.24 (m, 2H), 7.08 (d, 2H), 1H), 3.40 (br s, 1H), 1.67 (d, 3H). MS (ES+) m/z 430 (M+NH$_4^+$). Anal. Calc. for C$_{17}$H$_{14}$SO$_3$F$_6$: C, 49.52; H, 3.42. Found: C, 49.55; H, 3.28.

EXAMPLE 9

1,1,1,3,3,3-Hexafluoro-2-{4-[2-phenyl-1-(phenylsulfonyl)ethyl]phenyl}propan-2-ol

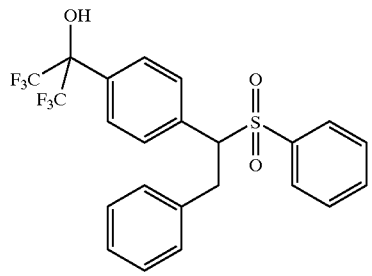

Prepared in the manner of Example 8 except benzyl bromide was substituted for iodomethane. Purification by flash chromatography (4:1 hexanes/EtOAc) afforded the title compound as a white solid (72%): mp=157° C. $^1$H NMR (CDCl$_3$) δ 7.50 (m, 5H), 7.32 (t, 2H), 7.14 (m, 5H), 6.97 (d, 2H), 4.30 (dd, 1H), 3.86 (dd, 1H), 3.48 (br s, 1H), 3.42 (dd, 1H). Anal. Calc. for C$_{23}$H$_{18}$O$_3$SF$_6$: C, 56.56; H, 3.17. Found: C, 56.41; H, 3.35. HRMS (M+NH$_4^+$) Calc.: 506.1225. Found: 506.1223.

EXAMPLE 10

1-Phenyl-2-(phenylsulfonyl)-2-{4-[2,2,2-trifluoro-1-hydroxy-1-(trifluoromethyl)ethyl]-phenyl}ethanone1

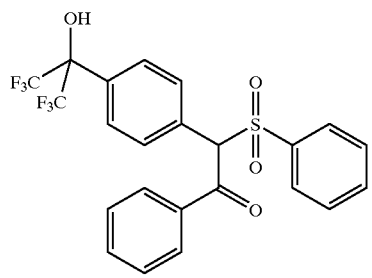

Prepared in the manner of Example 8 except benzoyl chloride was substituted for iodomethane. The product was isolated by reverse phase HPLC with a gradient elution (60:40H$_2$O-TFA:CH$_3$CN, λ=254 nM) as a white solid (15%): $^1$H NMR (CDCl$_3$) δ 7.84 (d, 2H), 7.51 (m, 6H), 7.38 (m, 4H), 7.31 (t, 2H), 6.12 (s, 1H). MS (ES+) m/z 503 (MH$^+$).

EXAMPLE 11

3,3-Dimethyl-1-(phenylsulfonyl)-1-{4-[2,2,2-trifluoro-1-hydroxy-1-(trifluoromethyl) -ethyl]phenyl}butan-2-one

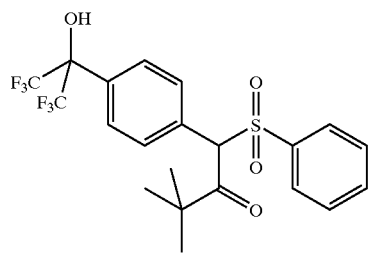

Prepared in the manner of Example 8 except trimethylacetyl chloride was substituted for iodomethane. The product was isolated by flash chromatography (10:1 hexanes/EtOAc) as a white solid (44%): mp=172° C. $^1$H NMR (CDCl$_3$) δ 7.52 (m, 3H), 7.40 (d, 2H), 7.27 (m, 4H), 5.61 (s, 1H), 1.05 (s, 9H). Anal. Calc. for C$_{21}$H$_{20}$O$_4$SF$_6$: C, 52.28; H, 4.18. Found: C, 51.90; H, 4.09. HRMS (M+NH$_4^+$) Calc.: 483.1065. Found: 483.1064.

EXAMPLE 12

1-(4-Chlorophenyl)-2-(phenylsulfonyl)-2-{4-[2,2,2-trifluoro-1-hydroxy-1-(trifluoromethyl)ethyl]phenyl}ethanone

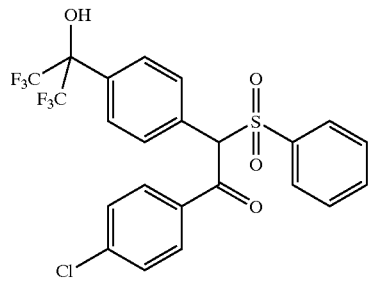

Prepared in the manner of Example 8 except 4-chlorobenzoyl chloride was substituted for iodomethane. Purification by reverse phase HPLC using a gradient elution of 60:40H$_2$O/TFA:CH$_3$CN to 0:100H$_2$O/TFA:CH$_3$CN at 254 nm afforded the title compound as a white solid (66%). $^1$H NMR (CDCl$_3$) δ 7.78 (d, 2H), 7.51 (m, 5H), 7.34 (m, 6H), 6.05 (s, 1H). MS (ES+) m/z 537 (MH$^+$).

EXAMPLE 13

1-(4-Methoxyphenyl)-2-(phenylsulfonyl)-2-{4-[2,2,2-trifluoro-1-hydroxy-1-(trifluoromethyl)ethyl]phenyl}ethanone

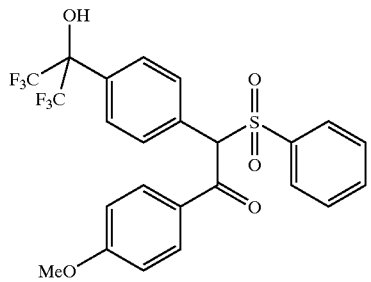

Prepared in the manner of Example 8 except 4-methoxybenzoyl chloride was substituted for iodomethane. Purification by reverse phase HPLC using a gradient elution of 60:40H$_2$O/TFA:CH$_3$CN to 0:100H$_2$O/TFA:CH$_3$CN at 254 nm afforded the title compound as a white solid (58%): mp=59° C. $^1$H NMR (CDCl$_3$) δ 7.42 (t, 5H), 7.26 (t, 2H), 7.08 (d, 2H), 6.81 (d, 2H), 6.60 (d, 2H), 4.17 (m 1H), 3.73 (m, 1H), 3.62 (s, 3H), 3.30 (m, 1H). HRMS (M$^+$) Calc.: 518.0987. Found: 518.1008.

EXAMPLE 14

1,1,1,3,3,3-Hexafluoro-2-{4-[1-(phenylsulfonyl)but-3-enyl]phenyl}propan-2-ol

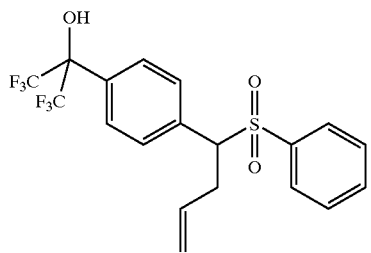

Tert-Butyl(dimethyl)[2,2,2-trifluoro-1-{4-[(phenylsulfonyl)methyl]phenyl}-1-(trifluoromethyl)ethoxy]silane (378 mg, 0.74 mmol) was dissolved in anhydrous THF (10 mL) under argon and cooled to −78° C. 1.6M BuLi solution in hexanes (0.5 mL, 0.85 mmol) was added and the reaction was allowed to warm to 0° C. After 30 min at 0° C., the reaction was cooled to −78° C. and DMPU (0.26 mL, 2.1 mmol) was added, followed by allyl bromide (0.07 mL, 0.81 mmol). The reaction was allowed to warm to 0° C. and monitored by thin layer chromatography. The reaction was quenched with saturated NH$_4$Cl and diluted with ethyl acetate. The layers were separated and the organic phase was washed with brine, dried (MgSO$_4$), and concentrated in vacuo. Purification by flash chromatography (6:1 hexanes/EtOAc) afforded the protected sulfone as a colorless oil. The sulfone was deprotected as described in Example 2 step 3. Purification by flash chromatography (6:1 hexanes/EtOAc) afforded the title compound as a white solid (266 mg, 82%): mp=148° C. $^1$H NMR (CDCl$_3$) δ 7.55 (m, 3H), 7.45 (d, 2H), 7.33 (t, 2H), 7.17 (d, 2H), 5.55 (m, 1H), 5.04 (m, 2H), 4.14 (dd, 1H), 3.51 (br s, 1H), 3.21 (m, 1H), 2.93 (m, 1H). Anal. Calc. for C$_{19}$H$_{16}$O$_3$SF$_6$: C, 52.06; H, 3.68. Found: 52.04; H, 3.45. HRMS (M+NH$_4$$^+$) Calc.: 456.1068. Found: 456.1075.

EXAMPLE 15

1,1,1,3,3,3-Hexafluoro-2-{4-[1-(phenylsulfonyl)propyl]phenyl}propan-2-ol

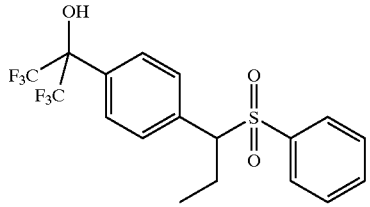

Prepared in the manner of Example 14 except iodoethane was substituted for allyl bromide. Purification by flash chromatography (6:1 hexanes/EtOAc) afforded the title compound as a white solid (25%): mp=148° C. $^1$H NMR (CDCl$_3$) δ 7.55 (m, 3H), 7.41 (d, 2H), 7.33 (t, 2H), 7.17 (d, 2H), 3.99 (dd, 1H), 3.48 (br s, 1H), 2.52 (m 1H), 2.17 (m, 1H), 0.89 (t, 3H). Anal. Calc. for C$_{18}$H$_{16}$O$_3$SF$_6$: C, 50.71; H, 3.78. Found: C, 50.75; H, 3.47. HRMS (M$^+$NH$_4$$^+$) Calc.: 444.1068. Found: 444.1082.

EXAMPLE 16

1,1,1,3,3,3-Hexafluoro-2-{4-[3,3,3-trifluoro-1-(phenylsulfonyl)propyl]phenyl}propan-2-ol

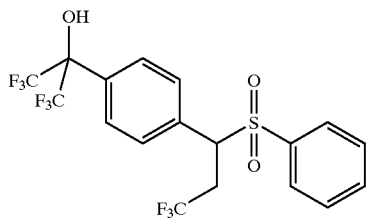

Prepared in the manner of Example 14 except 2-iodo-1,1,1-trifluoroethane was substituted for allyl bromide. Purification by flash chromatography (10:1 hexanes/EtOAc) afforded the title compound as a white solid (50%): mp=151° C. $^1$H NMR (CDCl$_3$) δ 7.51 (m, 3H), 7.36 (d, 2H), 7.27 (t, 2H), 7.11 (d, 2H), 4.26 (dd, 1H), 3.49 (br s, 1H), 3.26 (m, 1H), 2.97 (m, 1H). Anal. Calc. for C$_{18}$H$_{13}$O$_3$SF$_9$: C, 45.01; H, 2.73. Found: C, 45.17; H, 2.61. HRMS (M+NH$_4$$^+$) Calc.: 498.0782. Found: 498.0785.

EXAMPLE 17

1,1,1,3,3,3-Hexafluoro-2-{4-[2-(4-methylphenyl)-1-(phenylsulfonyl)ethyl]phenyl}propan-2-ol

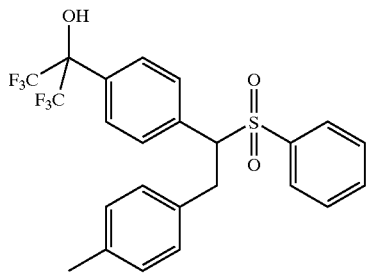

Prepared in the manner of Example 14 except α-chloro-p-xylene was substituted for allyl bromide. Purification by reverse phase HPLC using a gradient elution of 60:40H$_2$O/TFA:CH$_3$CN to 0:100H$_2$O/TFA:CH$_3$CN at 254 nm afforded the title compound as a white solid (15%): mp=159° C. $^1$H NMR (CDCl$_3$) δ 7.42 (m, 5H), 7.25 (t, 2H), 7.10 (d, 2H), 6.87 (d, 2H), 6.79 (d, 2H), 4.21 (dd, 1H), 3.74 (dd, 1H), 3.42 (br s, 1H), 3.31 (m, 1H), 2.15 (s, 3H). Anal. Calc. for C$_{24}$H$_{20}$O$_3$SF$_6$: C, 57.37; H, 4.01. Found: C, 57.16; H, 4.30. HRMS (M$^+$) Calc.: 502.1037. Found: 502.1066.

EXAMPLE 18

2-{4-[2-(1,1'-Biphenyl-4-yl)-1-(phenylsulfonyl)ethyl]phenyl}-1,1,1,3,3,3-hexafluoropropan-2-ol

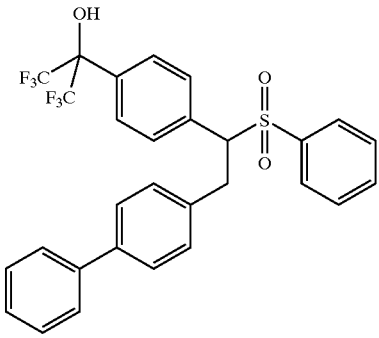

Prepared in the manner of Example 14 except 4-(chloromethyl)biphenyl was substituted for allyl bromide. Purification by reverse phase HPLC using a gradient elution of 60:40H$_2$O/TFA:CH$_3$CN to 0:100H$_2$O/TFA:CH$_3$CN at 254 nm afforded the title compound as a white solid (17%): mp=192° C. $^1$H NMR (CDCl$_3$) δ 7.43 (m, 7H), 7.28 (m, 7H), 7.13 (d, 2H), 6.98 (d, 2H), 4.26 (dd, 1H), 3.83 (dd, 1H), 3.40 (m, 2H). Anal. Calc. for C$_{29}$H$_{22}$O$_3$F$_6$S: C, 61.70; H, 3.93. Found: C, 61.45; H, 4.05. HRMS (M$^+$) Calc.: 564.1194. Found: 564.1238.

EXAMPLE 19

1,1,1,3,3,3-Hexafluoro-2-{4-[1-methyl-1-(phenylsulfonyl)ethyl]phenyl}propan-2-ol

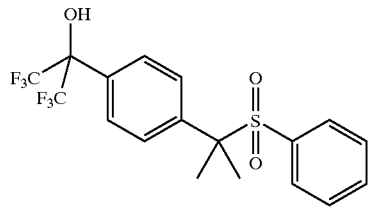

Tert-Butyl(dimethyl)[2,2,2-trifluoro-1-{4-[(phenylsulfonyl)methyl]phenyl}-1-(trifluoromethyl)ethoxy]silane (436 mg, 0.85 mmol) was dissolved in anhydrous THF (6 mL) under argon and cooled to −78° C. 1.6M BuLi solution in hexanes (0.56 mL, 0.89 mmol) was added and the reaction was allowed to warm to room temperature. After stirring at ambient temperature for 15 minutes, the reaction was cooled to −78° C. and iodomethane was added (0.06 mL, 0.96 mmol). After warming to 0° C. and stirring for 15 minutes, the reaction was again cooled to −78° C., and the alkylation procedure repeated. The reaction was quenched with H$_2$O and diluted with ethyl acetate. The layers were separated and the organic phase was washed with brine, dried (MgSO$_4$), and concentrated in vacuo. Purification by flash chromatography (10:1 hexanes/EtOAc) afforded the protected sulfone as a colorless oil. The sulfone was deprotected as described in Example 2 step 3. Purification by flash chromatography (6:1 hexanes/EtOAc) afforded the title compound as a white solid (76 mg, 21%): mp=185° C. $^1$H NMR (CDCl$_3$) δ 7.54 (d, 2H), 7.45 (m, 1H), 7.36 (d, 2H), 7.22 (m, 4H), 3.46 (br s, 1H), 1.77 (s, 6H). Anal. Calc. for C$_{18}$H$_{16}$O$_3$SF$_6$: C, 50.71; H, 3.78. Found: C, 50.66; H, 3.69. HRMS (M+NH$_4^+$) Calc.: 444.1068. Found 444.1090.

EXAMPLE 20

LXR Reporter Gene Transactivation Assay

Human hepatic cells (Huh-7) were cotransfected with a luciferase reporter gene (pGal4-RE), where transcription of luciferase gene is driven by the Gal4 response element, and a chimeric gene construct of liver X receptor (Gal4$_{DBD}$-LXRα$_{LBD}$ or Gal4$_{DBD}$-LXRβ$_{LBD}$), which comprises a DNA sequence that encodes a hybrid protein of LXR ligand binding domain (LXR$_{LBD}$) and Gal4 DNA-binding domain (Gal4$_{DBD}$). The transfection was performed in culture dishes using LipofectAMINE2000 reagent. The transfected cells were harvested 20 hr later and resuspended in assay medium containing RPMI 1640 medium, 2% fetal bovine lipoprotein deficient serum, 100 units/ml pencillin and 100 μg/ml streptomycin.

In screening for LXR agonists, the transfected cells were dispensed in an assay plate (384-well white tissue culture plate) containing the test compounds at 10 μM final concentration and incubated for 24 hr. The effects of test compounds on the activation of LXR$_{LBD}$ and hence luciferase transcription was determined by measuring the luciferase activity using Steady-Glo luciferase assay substrate. Luciferase activity results are expressed as the fold-induction relative to DMSO controls. Compounds that exhibited >10 fold induction were then retested and the EC$_{50}$ was determined as the concentration necessary to produce 50% of the maximal luciferase activity. Each of the compounds of Examples 1–19 was found to have an EC$_{50}$ of less than 50 μM.

What is claimed is:

1. A compound corresponding to Formula (I):

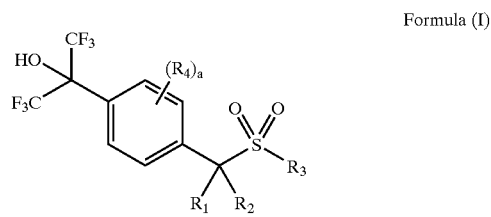

Formula (I)

wherein:

R$_1$ and R$_2$ are independently hydrogen or optionally substituted alkyl, alkenyl, aryl, acyl, or alkaryl;

R$_3$ is optionally substituted alkyl or aryl;

each R$_4$ is independently hydrogen, alkyl, aryl, heteroaryl, hydroxy, alkoxy, cyano, nitro, amino, alkenyl, alkynyl, amido, alkylcarbonyl, alkoxycarbonyl, aryloxycarbonyl, haloalkylcarbonyl, alkylthiocarbonyl, arylthiocarbonyl, alkyl optionally substituted with one or more substituent selected from lower alkyl, halogen, hydroxyl, haloalkyl, cyano, nitro, carboxyl, amino, alkoxy and aryl, or aryl optionally substituted with one or more substituent selected from hydrogen, halogen, haloalkyl, hydroxy, lower alkyl, alkoxy, methylene dioxy, ethylenedioxy, cyano, nitro, alkylthio, alkylsulfonyl, sulfonic acid, sulfonamide, amino, aryl and heteroaryl; and a is 0–4.

2. A compound of claim 1 wherein a is 0 or 1, and at least one of $R_1$ and $R_2$ is hydrogen.

3. A compound of claim 1 wherein, a is 0 and $R_1$ and $R_2$ are both hydrogen.

4. A compound of claim 1 wherein, a is 0, one of $R_1$ and $R_2$ is hydrogen, and the other of $R_1$ and $R_2$ is other than hydrogen.

5. A compound of claim 1 wherein $R_1$ is methyl, ethyl, biphenyl, trifluoroethyl, $CH_2CHCH_2$-, methoxy, $(CH_3)_3CO$—, benzyl, or halo or alkoxy substituted benzyl.

6. A compound of claim 5 wherein $R_2$ is hydrogen.

7. A compound of claim 5 wherein $R_2$ is alkyl.

8. A compound of claim 5 wherein $R_3$ is phenyl or halo, alkyl or alkoxy substituted phenyl.

9. A compound of claim 5 wherein $R_3$ is naphthyl.

10. A compound of claim 1 wherein $R_3$ is phenyl or halo, alkyl or alkoxy substituted phenyl.

11. A compound of claim 1 wherein $R_3$ is naphthyl.

12. A compound selected from compounds of the group consisting of 1,1,1,3,3,3-Hexafluoro-2-{4-[(phenylsulfonyl)methyl]phenyl}propan-2-ol;

1,1,1,3,3,3-Hexafluoro-2-(4-{[(4-methylphenyl)sulfonyl]methyl}phenyl)propan-2-ol;

1,1,1,3,3,3-Hexafluoro-2-{4-[(2-naphthylsulfonyl)methyl]phenyl}propan-2-ol;

2-(4-{[(4-Bromophenyl)sulfonyl]methyl}phenyl)-1,1,1,3,3,3-hexafluoropropan-2-ol;

2-(4-{[(2-Bromophenyl)sulfonyl]methyl}phenyl)-1,1,1,3,3,3-hexafluoropropan-2-ol;

2-(4-{[(3-Bromophenyl)sulfonyl]methyl}phenyl)-1,1,1,3,3,3-hexafluoropropan-2-ol;

2-(4-{[(4-Chlorophenyl)sulfonyl]methyl}phenyl)-1,1,1,3,3,3-hexafluoropropan-2-ol;

1,1,1,3,3,3-Hexafluoro-2-{4-[1-(phenylsulfonyl)ethyl]phenyl}propan-2-ol;

1,1,1,3,3,3-Hexafluoro-2-{4-[2-phenyl-1-(phenylsulfonyl)ethyl]phenyl}propan-2-ol;

1-Phenyl-2-(phenylsulfonyl)-2-{4-[2,2,2-trifluoro-1-hydroxy-1-(trifluoromethyl)-ethyl]-phenyl}ethanone;

3,3-Dimethyl-1-(phenylsulfonyl)-1-{4-[2,2,2-trifluoro-1-hydroxy-1-(trifluoromethyl)-ethyl]phenyl}butan-2-one;

1-(4-Methoxyphenyl)-2-(phenylsulfonyl)-2-{4-[2,2,2-trifluoro-1-hydroxy-1-(trifluoromethyl)ethyl]phenyl}ethanone;

1,1,1,3,3,3-Hexafluoro-2-{4-[1-(phenylsulfonyl)but-3-enyl]phenyl}propan-2-ol;

1,1,1,3,3,3-Hexafluoro-2-{4-[1-(phenylsulfonyl)propyl]phenyl}propan-2-ol;

1,1,1,3,3,3-Hexafluoro-2-{4-[3,3,3-trifluoro-1-(phenylsulfonyl)propyl]phenyl} propan-2-ol;

1-(4-Chlorophenyl)-2-(phenylsulfonyl)-2-{4-[2,2,2-trifluoro-1-hydroxy-1-(trifluoromethyl)ethyl]phenyl}ethanone;

1,1,1,3,3,3-Hexafluoro-2-{4-[2-(4-methylphenyl)-1-(phenylsulfonyl)ethyl]-phenyl}propan-2-ol;

2-{4-[2-(1,1'-Biphenyl-4-yl)-1-(phenylsulfonyl)ethyl]phenyl}-1,1,1,3,3,3-hexa-fluoropropan-2-ol; and 1,1,1,3,3,3-Hexafluoro-2-{4-[1-methyl-1-(phenylsulfonyl)ethyl]phenyl}propan-2-ol.

* * * * *